United States Patent [19]
Dong et al.

[11] Patent Number: 6,037,522
[45] Date of Patent: Mar. 14, 2000

[54] AGROBACTERIUM-MEDIATED TRANSFORMATION OF MONOCOTS

[75] Inventors: Jinjiang Dong; Weimin Teng; Timothy C. Hall, all of College Station, Tex.

[73] Assignee: Rhone-Poulenc Agro, Lyons, France

[21] Appl. No.: 09/103,084

[22] Filed: Jun. 23, 1998

[51] Int. Cl.[7] .......................... C12N 15/29; C12N 15/82; C12N 15/00; A01H 4/00; A01H 5/00
[52] U.S. Cl. .......................... 800/278; 800/295; 800/298; 536/24.1; 435/419; 435/468; 435/320.1
[58] Field of Search ..................... 800/278, 295, 800/298; 536/24.1; 435/419, 468, 320.1

[56] References Cited

U.S. PATENT DOCUMENTS

| | | |
|---|---|---|
| 5,177,010 | 1/1993 | Goldman et al. . |
| 5,187,073 | 2/1993 | Goldman et al. . |
| 5,591,616 | 1/1997 | Hiei et al. . |
| 5,712,135 | 1/1998 | D'Halluin et al. . |

OTHER PUBLICATIONS

Boulter et al. plant Science, 70, pp. 90–99, 1990.
Rashid et al. Plant Cell Reports, 15, pp. 727–730, 1996.
Barcelo et al. The Plant Journal, 5(4), pp. 583–592, 1994.
Barcelo et al. (1994) *The Plant Journal* 5:583.
Chan et al. (1993) *Plant Mol. Biol.* 22:491.
Christou (1997) *Plant Mol. Biol.* 35:197.
Hiei et al. (1994) *Plant Journal* 6:271.
Liu et al. (1992) *Plant Mol. Biol.* 20:1071.
Park et al. (1996) *Plant Mol. Biol.* 32:1135.
Vijayachandra et al. (1995) *Plant Mol. Biol.* 29:125.

*Primary Examiner*—Lynette R. F. Smith
*Assistant Examiner*—Thomas Haas
*Attorney, Agent, or Firm*—Bakerbotts, LLP

[57] ABSTRACT

The present invention provides methods of Agrobacterium-mediated transformation of monocots. The invention further provides methods of making transgenic monocots, as well as transgenic monocots made by the present methods, and seeds and progeny thereof.

26 Claims, 3 Drawing Sheets

AGROBACTERIUM-MEDIATED TRANSFORMATION OF MONOCOTS

BACKGROUND OF THE INVENTION

The soil bacterium *Agrobacterium tumefaciens* infects many species of dicotyledonous plants (dicots) and induces tumors called crown galls. The capacity of Agrobacterium to induce crown galls resides in its tumor-inducing (Ti) plasmid, which functions by transferring a region of the plasmid known as T-DNA into the host plant genome. The T-DNA is flanked by 24 base pair direct repeats which are required for transfer of the T-DNA to the host plant genome. The Agrobacterium plasmid T-DNA between the repeats can be deleted and replaced by genes of interest to provide a disarmed Agrobacterium useful for gene transfer into dicots.

Agrobacterium-mediated gene transfer is widely used for production of transgenic dicots. Generally, plant cells are transformed using Agrobacterium, and the transformed cells are regenerated into transgenic plants. Depending upon the plant species, the transformed cells may be derived from leaves, roots, hypocotyls, petioles, cotyledons, or seeds.

Transgenic dicots may also be obtained by an in planta transformation method, in which germinating seeds or wounded plants are inoculated with Agrobacterium, and plants are grown to maturity and seeds collected. An in planta transformation method has been used for Agrobacterium-mediated transformation of the dicot *Arabidopsis thaliana*. (Bechtold et al. (1993) *Life Sci.* 316:1194, C.R. Acad. Sci. Paris; Bechtold et al. in *Gene Transfer to Plants*, Potrykus et al., eds., Springer-Verlag Berlin, 1995, p. 19.) Vacuum infiltration with an Agrobacterium suspension was used to inoculate Arabidopsis plants at the panicle initiation stage. Plants were then transferred to soil, and seeds were collected from the inoculated plants. As many as ten independently-transformed plants can reportedly be derived from a single vacuum-infiltrated Arabidopsis plant. Bechtold et al., id., suggest that the success of the vacuum-infiltration transformation method as applied to Arabidopsis may be due to particular aspects of Arabidopsis biology, including the size of the plant, cycle length, and reproductive biology, which may prevent the method from being applied to other species.

Monocotyledonous plants (monocots) are generally less susceptible than dicots to Agrobacterium-mediated transformation, and thus direct DNA transfer methods have been widely used for monocot transformation. Direct DNA transfer methods include naked DNA uptake stimulated by polyethylene glycol or electroporation, and particle gun transformation. See, e.g., *Gene Transfer to Plants*, Potrykus et al., eds., Springer-Verlag, Berlin, 1995. For example, de la Peña (1987) *Nature* 325:272 report transformation by injection of DNA into floral tillers of rye plants. However, direct DNA transfer methods suffer deficiencies including frequent incorporation of the DNA into the host genome as multiple rearranged copies of the desired gene together with flanking sequences from the plasmid vector. These rearrangement and integration events may result in gene expression that is aberrant and unstable in $R_0$ and progeny plants.

Agrobacterium-mediated gene transfer usually results in the insertion of a discrete, unrearranged DNA segment into the host genome, and thus it would be desirable to develop methods for the Agrobacterium-mediated transformation of monocots. Although monocots are considered to be relatively recalcitrant to transformation with Agrobacterium, there are various reports of gene transfer into monocots by Agrobacterium-mediated transformation (Boulton et al. (1989) *Plant Mol. Biol.* 12:31; Chan et al. (1992) *Plant Cell Physiol.* 33:577; Gould et al. (1991) *Plant Physiol.* 95:426; Graves et al. (1986) *Plant Mol. Biol.* 7:43; Grimsley et al. (1987) *Nature* 325:177; Raineri et al. (1990) *Bio/Technology* 8:33; U.S. Pat. No. 5,177,010 to Goldman et al. and U.S. Pat. No. 5,187,073 to Goldman et al.). However, many of these early studies of Agrobacterium-mediated transformation of monocots have been subject to controversy (Potrykus (1990) *Bio/Technology* 8:5350) and many have not been independently confirmed.

More recent studies report successful Agrobacterium-mediated transformation of rice. Hiei et al. (1994) *Plant J.* 6:271 disclose Agrobacterium-mediated transformation of Japonica rice. Various tissues from rice, including shoot apices, scutella, immature embryos, calli induced from young roots and scutella, and cells in suspension cultures induced from scutella were co-cultivated with *A. tumefaciens*, resulting in various levels of reporter transgene expression in these tissues. Transgenic plants were recovered from scutellum-derived calli that has been co-cultivated with *A. tumefaciens*. Stable integration, expression, and inheritance of transgenes was reported in $R_0$, $R_1$ and $R_2$ generations.

U.S. Pat. No. 5,591,616 to Hiei et al. discloses a method for transforming a monocot comprising transforming a cultured tissue during the dedifferentiation process, or a dedifferentiated cultured tissue, with Agrobacterium. The cultured tissue is obtained by culturing an explant for not less than seven days on a dedifferentiation-inducing medium.

Dong et al. (1996) *Molecular Breeding* 2:267 report Agrobacterium-mediated transformation of Javanica rice. Co-cultivation of scutellar calli with *A. tumefaciens* resulted in transgenic fertile plants. The transgenes were transmitted to the $R_1$ and $R_2$ generations.

The foregoing methods of Agrobacterium-mediated transformation of rice involve the use of scutellar tissues or scutellar-derived callus, and involve relatively long-term in vitro selection procedures in tissue culture following the transformation process. Tissue culture manipulations have been associated with induction of somaclonal variation (Kaeppler et al. (1993) *Proc. Natl. Acad. Sci. USA* 90:8773; Phillips et al. (1994) *Proc. Natl. Acad. Sci. USA* 91:5222). Alternate methods of monocot transformation are desirable, for example to permit the use of tissue culture-recalcitrant cultivars and to reduce the incidence of somaclonal variations associated with the tissue culture process.

In accordance with the present invention, an Agrobacterium-mediated transformation method utilizing inflorescence of monocots as the target tissue has been developed.

SUMMARY OF THE INVENTION

The present invention provides a method of transforming a monocot comprising co-cultivating a monocot inflorescence or an inflorescence-derived callus with Agrobacterium containing a plasmid comprising a heterologous nucleic acid.

In one embodiment, the present invention provides a method of transforming a monocot comprising dissecting an inflorescence from a monocot, initiating a callus from the inflorescence to generate an inflorescence-derived callus, and co-cultivating the inflorescence-derived callus with Agrobacterium containing a plasmid comprising a heterologous nucleic acid.

In another embodiment, the present invention provides a method of transforming a monocot comprising dissecting an inflorescence from a monocot, and co-cultivating the inflorescence with Agrobacterium containing a plasmid comprising a heterologous nucleic acid.

In another embodiment, the present invention provides a method of making a transgenic monocot comprising dissecting an inflorescence from a monocot, initiating a callus from the inflorescence to generate an inflorescence-derived callus, co-cultivating the inflorescence-derived callus with Agrobacterium containing a plasmid comprising a heterologous nucleic acid, and regenerating a transgenic monocot from the callus.

Yet another method of making a transgenic monocot comprises dissecting an inflorescence from a monocot, co-cultivating the inflorescence with Agrobacterium containing a plasmid comprising a heterologous nucleic acid, initiating a callus from the inflorescence and regenerating a transgenic monocot from the callus.

The present invention further provides transgenic monocots provided by the methods of the invention, and the seeds and progeny of the transgenic monocots.

BRIEF DESCRIPTION OF THE DRAWINGS

FIG. 1A shows a fertile rice spikelet immediately before anthesis. FIG. 1B shows a primary and secondary rachis-branch, bearing a spikelet. FIG. 1C shows a panicle bearing multiple rachis-branch and spikelets.

DETAILED DESCRIPTION OF THE INVENTION

The present invention provides methods of transforming a monocot, methods of producing transgenic monocots, plants produced by the methods of the invention, and seeds and progeny of such plants. The methods of the present invention involve Agrobacterium-mediated transformation in which the target tissue for transformation is the monocot inflorescence. The present methods overcome the deficiencies associated with monocot transformation by direct DNA transfer methods, including undesirable rearrangement and integration events. In addition, the present methods reduce difficulties associated with other methods of Agrobacterium-mediated monocot transformation, such as somatic variation associated with lengthy in vitro culture. In particular, by utilizing inflorescence as the target tissue, the present methods decrease the length of in vitro culture required by methods utilizing other target tissue, for example scutellar tissue.

The present methods and transgenic monocots are useful in the production of plants with altered and improved properties, and in the production of plants having selectable markers and proprietary tags.

In accordance with the present invention, a monocot is defined as any of a class or subclass of seed plants having an embryo with a single cotyledon. In a preferred embodiment of the present invention, the monocot is a member of the family Gramineae including the cereals rice, corn, wheat, barley, oats and rye. In a particularly preferred embodiment, the monocot is rice.

Figure 1A:
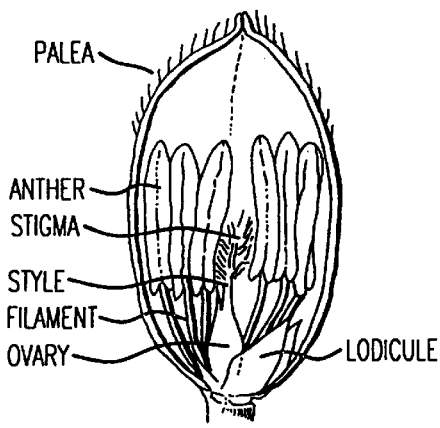
FIGS. 1A–C depict the morphology of a gramineous inflorescence and are modified from Hoshikawa (1989) "The growing rice plant: an anatomical monograph" Nobunkyo, Tokyo, pp 208 and 240.
Figure 1B:
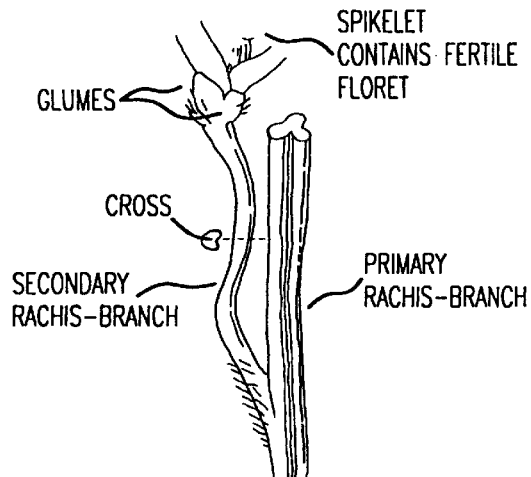
Figure 1C:
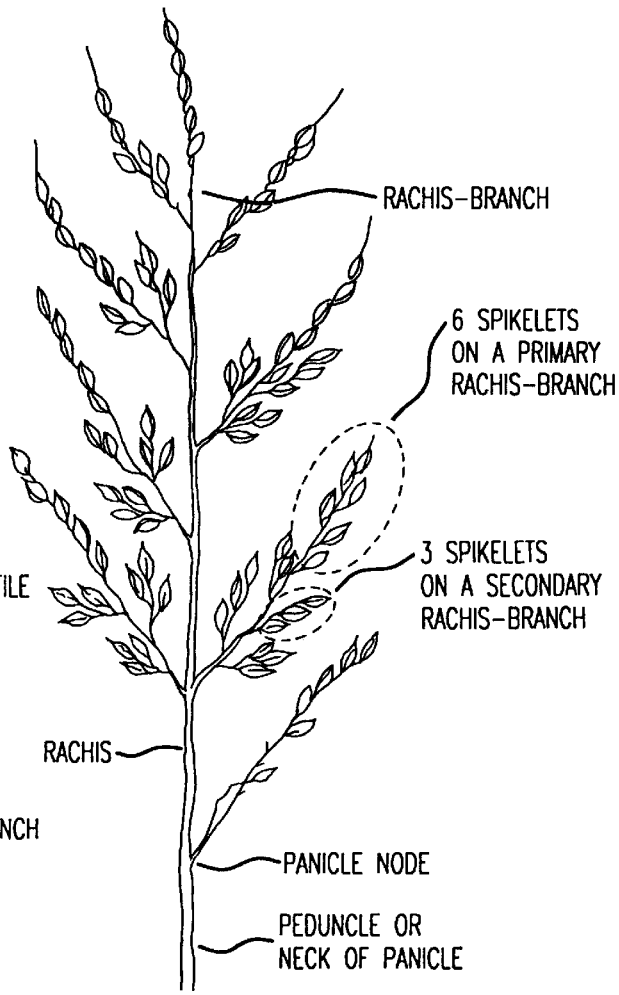

The target tissue for Agrobacterium-mediated transformation in the methods of the present invention is the inflorescence. An inflorescence is structural entity of a plant comprising a floral axis with its appendages. The basic inflorescence unit of the monocots of the family Gramineae is a spikelet containing one or more sessile florets, as depicted in FIG. 1A. At the base of the spikelet are two bracts, as shown in FIG. 1B. The arrangement of spikelets on the axis, or rachis, defines the gross inflorescence type as a spike, raceme, or panicle. For example, the inflorescence of rice is a panicle bearing hundreds of flowers.

It has been discovered in accordance with the present invention that the monocot inflorescence may be transformed at a developmental stage from immature to mature. Inflorescence at the immature stage, i.e. prior to emergence from the leaf sheath, or boot, is preferred as the target tissue for transformation by the present methods. For in vitro transformation methods, the inflorescence may be dissected and transferred to culture media.

The present methods of transformation utilize Agrobacterium containing a plasmid comprising a heterologous nucleic acid. Genetically engineered Agrobacterium strains used for gene transfer to dicots are also useful for gene transfer to monocots. Agrobacterium-mediated gene transfer to dicots is well-known to those of ordinary skill in the art, and described for example in Gene Transfer to Plants, Potrykus et al., eds., Springer-Verlag, Berlin 1995, the disclosure of which is incorporated herein by reference. Generally, plant transformation vectors are derived by modifying the natural gene transfer systems of Agrobacterium tumefaciens or Agrobacterium rhizogenes.

The natural A. tumefaciens system comprises large Ti (tumor-inducing) plasmids containing a large segment, known as T-DNA, which is transferred to transformed plants. Another segment of the Ti plasmids, the vir region, is responsible for T-DNA formation and transfer. The T-DNA region is bordered by terminal repeats. In engineered disarmed A. tumefaciens strains, the tumor-inducing genes have been deleted, and the functions of the vir region are utilized to transfer heterologous DNA flanked by the T-DNA border sequences. The T-DNA region generally also contains a selectable marker, a screenable marker, and a multiple cloning site for inserting the heterologous sequence to be transferred. The vir region and the T-DNA may be carried on the same or different plasmids. Such genetically engineered strains allow the efficient transfer of sequences bordered by the T-region into the nuclear genomes of plants.

The natural A. rhizogenes system comprises Ri (root-inducing) plasmids carrying T-DNA. A. rhizogenes strains have been similarly engineered to contain binary vectors having T-DNA containing a selectable marker, a screenable maker and a heterologous sequence.

In a preferred embodiment of the present invention, an engineered A. tumefaciens strain is used for transformation. Such strains are well-known to those of ordinary skill in the art, and many are commercially available. Representative engineered Agrobacterium strains are disclosed in the art, for example by Dong et al. (1996) Molecular Breeding 2:207; Chan et al. (1993) Plant Molecular Biology 22:491; Park et al. (1996) Plant Molecular Biology 32:1135; Hiei et al. (1994) Plant Journal 6:271; and U.S. Pat. No. 5,591,616, the disclosures of which are incorporated herein by reference. In a preferred embodiment, the present methods utilize an Agrobacterium strain such as LBA4404 (described by Hoekema et al. (1983) *Nature* 303:179, incorporated herein by reference) containing a binary vector (i.e., a vector in which the heterologous DNA is contained within the T-DNA border repeats and that can be episomally propagated in *E. coli* and Agrobacterium) and an extra copy of a DNA fragment encoding vir genes (for example as described by Jin et al. (1987) *J. Bacteriology* 169:4417, incorporated herein by reference).

The Agrobacterium used in the methods of the present invention contains a plasmid comprising a heterologous nucleic acid. In a preferred embodiment, the Agrobacterium is *A. tumefaciens*. Preferably, the heterologous nucleic acid is present between the T-DNA border repeats of a vector, for example a binary vector. In another embodiment, the hetrologous nucleic acid is present on a separate plasmid and introduced into the Agrobacterium by recombination. The vir region may be present on the plasmid comprising the heterologous nucleic acid, or on a separate plasmid. A plasmid comprising a heterologous nucleic acid may be introduced into Agrobacterium by conventional methods, including, for example, triparental mating. Such methods are known in the art and disclosed, for example by Fütterer in *Gene Transfer To Plants*, Potrykus et al. eds, Springer-Verlag, Berlin, 1995, p. 307, and Jin et al. (1987) *J. Bacteriol.* 169: 4417, the disclosures of which are incorporated herein by reference.

In accordance with the present invention, the heterologous nucleic acid is one which is not normally found in Agrobacterium T-DNA or the monocot that is to be transformed. As used herein, the term heterologous nucleic acid includes all synthetically engineered and biologically derived genes which may be introduced into a plant by genetic engineering, including but not limited to nonplant genes, modified genes, synthetic genes, portion of genes, and genes from monocots and other plant species. The heterologous nucleic acid preferably contains the coding region of a protein or polypeptide or antisense molecule of interest, with flanking regulatory sequences that promote the expression thereof in the resulting monocot.

Methods for constructing heterologous nucleic acids for successful transformations of plants are well known to those skilled in the art, and the same methods of construction may be utilized to produce the heterologous nucleic acids useful herein. Weising et al. (1988) *Annual Rev. Genet.* 22:241, the subject matter of which is incorporated herein by reference, describe suitable components which include promoters, polyadenylation sequences, selectable marker genes, reporter genes, enhancers, introns, and the like, and provide suitable references for compositions thereof. Sambrook et al. (1989) *Molecular Cloning: A Laboratory Manual*, Cold Spring Harbor, N.Y., provide suitable methods of construction.

Generally the plasmid comprising the nucleic acid heterologous gene will be relatively small, i.e. less than about 30 kb, to minimize any susceptibility to physical, chemical, or enzymatic degradation which is known to increase as the size of the gene increases.

Suitable heterologous nucleic acids for use herein include all nucleic acids that will provide or enhance a beneficial feature of the resultant transgenic monocot. For example, the nucleic acid may encode proteins or antisense RNA transcripts in order to promote increased food values, higher yields, pest resistance, disease resistance, and the like.

Representative nucleic acids include, for example, a bacterial dap A gene for increased lysine; Bt-endotoxin gene or protease inhibitor for insect resistance; lytic peptides genes for disease resistance, bacterial or plant EPSPS for resistance to glyphosate herbicide (U.S. Pat. Nos. 4,940,835, 5,188,642, 4,971,908, 5,145,783, 5,312,910, 5,633,435, 5,627,061, 5,310,667, WO 97/04103); bacterial or plant HPPD (WO 96/38567, WO 98/02562) for resistance to HPPD-inhibitor herbicides (i.e. diketones, isoxazoles, etc.), chitinase or glucan endo 1,3-B-glucosidase for fungicidal properties. Also, the nucleic acid may be introduced to act as a genetic tool to generate mutants and/or assist in the identification, genetic tagging, or isolation of segments of monocot genes. Additional examples may be found in Weising, supra.

The plasmid comprising the heterologous nucleic acid to be introduced into the plant further will generally contain either a selectable marker or a reporter gene or both to facilitate identification and selection of transformed cells. Alternatively, the selectable marker may be carried on a separate vector and used in a cotransformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al, supra. A preferred selectable marker gene is the hygromycin B phosphotransferase (hpt) coding sequence, which may be derived from *E. coli*. Other selectable markers known in the art include aminoglycoside phosphotransferase gene of transposon Tn5 (AphII) which encodes resistance to the antibiotics kanamycin, neomycin, and G418, as well as those genes which code for resistance or tolerance to glyphosate, bialaphos, methotrexate, imidazolinones, sulfonylureas, bromoxynil, dalapon, and the like. Selectable marker genes that confer herbicide tolerance are also of commercial utility in the resulting transformed plants.

Reporter genes which encode easily assayable marker proteins are well known in the art. In general, a reporter gene is a gene which is not present or expressed by the recipient organism or tissue and which encodes a protein whose expression is manifested by some easily detectable property, e.g. phenotypic change or enzymatic activity. Examples of such genes are provided in Weising et al, supra. Preferred genes include the chloramphenicol acetyl transferase (cat) gene from Tn9 of *E. coli*, the beta-gluronidase (gus) gene of the uidA locus of *E. coli*, the green fluorescence protein (GFP) gene from *Aequoria victoria*, and the luciferase (luc) gene from the firefly *Photinus pyralis*.

The regulatory sequences useful herein include any constitutive, inducible, tissue or organ specific, or developmental stage specific promoter which can be expressed in the particular plant cell. Suitable such promoters are disclosed in Weising et al, supra. The following is a partial representative list of promoters suitable for use herein: regulatory sequences from the T-DNA of *A. tumefaciens*, including mannopine synthase, nopaline synthase, and octopine synthase; alcohol dehydrogenase promoter from corn; light inducible promoters such as ribulose-biphosphate-carboxylase small subunit gene from a variety of species and the major chlorophyll a/b binding protein gene promoter; histone promoters (EP 507 698), actin promoters; maize ubiquitin 1 promoter (Christensen et al. (1996) *Transgenic Res.* 5:213); 35S and 19S promoters of cauliflower mosaic virus; developmentally regulated promoters such as the waxy, zein, or bronze promoters from maize; as well as synthetic or other natural promoters which are either inducible or constitutive, including those promoters exhibiting organ specific expression or expression at specific development stage(s) of the plant, like the alpha-tubulin promoter disclosed in U.S. Pat. No. 5,635,618.

Other elements such as introns, enhancers, polyadenylation sequences and the like, may also be present in the nucleic acid. These elements must be compatible with the remainder of the gene constructions. Such elements may or may not be necessary for the function of the gene, although they may provide a better expression or functioning of the gene by effecting transcription, stability of the mRNA, or the like. Such elements may be included in the nucleic acid as desired to obtain the optimal performance of the transforming gene in the plant. For example, the maize Adh1S first intron maybe placed between the promoter and the coding sequence of a particular heterologous nucleic acid. This intron, when included in a gene construction, is known to generally increase expression in maize cells of a protein. (Callis et al. (1987) *Genes Dev.* 1 :1183). Other suitable introns include the first intron of the shrunken-1 gene of maize (Maas et al. (1991) *Plant Mol. Biol.* 16:199); the first intron of the castor bean catalase (cat-1) gene (Ohta et al. (1990) *Plant Cell Physiol.* 31:805); potato catalase second intron of the ST-LSI gene (Vancanneyt et al. (1990) *Mol. Gen. Genet.* 220:245); tobacco yellow dwarf virus DSV intron (Morris et al. (1992) *Virology* 187:633; actin-1 (act-1) intron from rice (McElroy et al. (1990) *Plant Cell* 2:163); and triose phosphate isomerase (TPI) intron 1 (Snowden et al. (1996) *Plant Mol. Biol.* 31:689). However, sufficient expression for a selectable marker to perform satisfactorily can often by obtained without an intron. (Battraw et al. (1990) *Plant Mol. Biol.* 15:527).

The plasmid comprising the heterologous nucleic acid may also comprise sequences coding for a transit peptide, to drive the protein coded by the heterologous gene into the chloroplasts of the plant cells. Such transit peptides are well known to those of ordinary skill in the art, and may include single transit peptides, as well as multiple transit peptides obtained by the combination of sequences coding for at least two transit peptides. One preferred transit peptide is the Optimized Transit Peptide disclosed in U.S. Pat. No. 5,635, 618, comprising in the direction of transcription a first DNA sequence encoding a first chloroplast transit peptide, a second DNA sequence encoding an N-terminal domain of a mature protein naturally driven into the chloroplasts, and a third DNA sequence encoding a second chloroplast transit peptide.

To determine whether a particular combination of heterologous nucleic acid and recipient plant cells are suitable for use herein, the plasmid may include a reporter gene. An assay for expression of the reporter gene may then be performed at a suitable time after the heterologous nucleic acid has been introduced into the recipient cells. A preferred such assay entails the use of the *E. coli* beta-glucuronidase (gus) gene described by Jefferson et al. (1987) *EMBO J.* 6:3901, incorporated herein by reference.

In accordance with the methods of the present invention, a monocot is transformed by co-cultivating a monocot inflorescence or an inflorescence-derived callus with Agrobacterium containing a plasmid comprising a heterologous nucleic acid. In a preferred embodiment, the monocot is a gramineous plant such as rice, corn, wheat, barley oat, or rye. Agrobacterium-mediated transformation results in stable integration of the heterologous nucleic acid into the nuclear genome of a cell of the monocot.

Co-cultivation of a monocot inflorescence or inflorescence-derived callus with Agrobacterium is performed in vitro. In a method of transforming a monocot in which an inflorescence is co-cultivated with Agrobacterium containing a plasmid comprising a heterologous nucleic acid, inflorescences are dissected from the monocot. The inflorescence may be at any stage of development, although an immature inflorescence is preferred. The dissected inflorescences are co-cultivated with Agrobacterium containing a plasmid comprising a heterologous nucleic acid by contacting the inflorescences with Agrobacterium solution. In a preferred embodiment, the inflorescences are contacted with the Agrobacterium solution example for about 60 to about 80 hours at about 26° C. In a most preferred embodiment, inflorescences are contacted with the Agrobacterium solution example for about 72 hours at about 26° C. Co-cultivation of Agrobacterium and monocot inflorescences in vitro may be facilitated with vacuum infiltration, for example by applying a vacuum of about 1 mm Hg to about 5 mm Hg for about 5 to about 20 minutes. In a most preferred embodiment, a vacuum of about 2 mm Hg is applied for about 10 to about 15 minutes. Vacuum infiltration is preferably performed when contacting the inflorescences with Agrobacterium. The Agrobacterium-treated inflorescences are then placed on standard callus initiation/selective medium to generate inflorescence-derived calli, from which transgenic monocots are then generated by standard methods, for example as described by Dong et al, supra.

In a method of transforming a monocot in which an inflorescence is co-cultivated with Agrobacterium containing a plasmid comprising a heterologous nucleic acid, 1 0 inflorescences are dissected from a monocot and then placed on callus initiation medium to generate inflorescence-derived calli. In accordance with the present method, calli are generated from inflorescences by placing on callus initiation medium for from about three days to about sixty days. Calli may be generated by methods known in the art, for example as described by Buchholz et al (1998) in *Plant Virology Protocols: From Virus Isolation to Transgenic Resistance*, Foster et al., eds, Humana Press, Inc., Totowa, N.J., pp. 383–396, the disclosure of which is incorporated by reference. The inflorescence-derived calli are then co-cultivated with Agrobacterium by contacting the calli with Agrobacterium solution, for example for about fifteen to twenty minutes. Transgenic monocots are regenerated from the treated calli by standard methods, for example as described by Buchholz et al, ibid., at pp.397–416, incorporated herein by reference.

The Agrobacterium solution utilized in the foregoing methods of transforming a monocot comprises Agrobacterium containing a plasmid comprising a heterologous nucleic acid, as described herein, and liquid medium. To prepare a solution, Agrobacteria are grown in a standard culture medium which may contain one or more appropriate antibiotics for the particular construct. Culture media for Agrobacteria are known in the art and disclosed for example by Potrykus, supra. Agrobacterium are grown under standard growth conditions, for example from 2–3 days at 28° C. with selection on the appropriate antibiotics. Agrobacterium are then collected and resuspended in a co-cultivation medium to provide the Agrobacterium solution.

Media for co-cultivation with Agrobacterium are known in the art and disclosed for example by Potrykus, supra. For example, a suitable medium for co-cultivation is AAM (Hiei et al. (1994) *Plant J.* 6:271). Preferred co-cultivation media for vacuum infiltration are described by Bechtold et al. (1993) *Life Sci* 316: 1194 and Bent et al. (1994) *Science* 265:1856, the disclosures of which are incorporated herein by reference. In another preferred embodiment, the co-cultivation medium for vacuum infiltration additionally contains a wetting agent, for example Silwet®L-77 (OSi Specialities). The cocultivation medium also preferably contains acetosyringone, which is a known inducer of the vir region genes.

A representative medium for co-cultivation contains AA salts and amino acids (Toriyuma and Hinata (1985) *Plant Sci.* 41:179), MS vitamins (Murashige and Skoog (1962) *Physiol. Plant* 15:473), 0.5 g/L casamino acids, 68.5 g/L sucrose, 36.0 g/L glucose, and 100 μM acetosyringone, at pH 5.2

A representative co-cultivation medium for vacuum infiltration containing a wetting agent is described by Green at http://www.bch.msu.edu/pamgreen/vac.txt, and contains, in one liter of medium, 2.2 grams MS salts (Murashige and Skoog, Gibco), 1X B5 vitamins, 50 grams sucrose, 0.5 grams morpholinoethanesulfonic acid (MES), potassium hydroxide to pH 5.7, 0.044 μM benzylaminopurine, and 200 μl Silwet(®L-77.

The transformed inflorescence-derived calli produced by the in vitro transformation methods described above are used to regenerate transgenic monocots, and seeds and progeny thereof, by methods known in the art.

In each of the foregoing methods, successful transformation may be monitored by selection and screening. As described hereinabove, the engineered Agrobacterium strains used in the present methods generally contain a selectable marker gene that encodes a product that allows detoxification or evasion of a selective agent, such as an antibiotic or herbicide. Selection for transformants is accomplished by applying the appropriate selective agent to the culture medium, soil or plantlet in concentrations known in the art, and selecting inflorescences, calli, or plants that survive the selection agent. For example, putatively transformed monocots may be allowed to flower and set seeds, and seeds are germinated in selection medium to identify transformant seedlings.

Transformation may also be monitored by screening for the expression of a reporter gene or the heterologous nucleic acid. The screening method is dependent upon the product encoded by the reporter gene or heterologous nucleic acid. The heterologous nucleic acid may provide the screenable marker, or a nucleic acid encoding a screenable marker may be present in addition to the desired heterologous nucleic acid. Reporter genes encode products that can be directly detected, or that catalyze reactions having detectable products. Expression of reporter genes can often be measured visually or biochemically. Suitable reporter genes and detection methods useful in plants are well known in the art, and reviewed for example by Schrott in *Gene Transfer to Plants*, Potrykus et al., eds, Springer-Verlag, Berlin, 1995, p. 325, incorporated herein by reference.

Successful transformation of monocots by the present methods may also be confirmed by genomic analysis. For example, in Southern blot analysis, genomic DNA of putatively transformed plants is digested with restriction enzymes, fractionated on an agarose gel, blotted to a nitrocellulose membrane, and probed with a labeled DNA fragment of a plasmid in the Agrobacterium, for example a fragment from a gene encoding a selectable or screenable marker, or the heterologous nucleic acid. Additional methods of characterization of transgenic plants by molecular analysis, for example by Northern blot analysis, immunoblot analysis, and PCR amplification, are also known in the art, and described for example by Buchholz et al (1998) in *Plant Virology Protocols: From Virus Isolation to Transgenic Resistance*, Foster et al., eds, Humana Press, Inc., Totowa, N.J., pp. 383–396, incorporated herein by reference.

All of the references cited herein are incorporated by reference in their entirety.

EXAMPLE I

Methods

Figure 2:
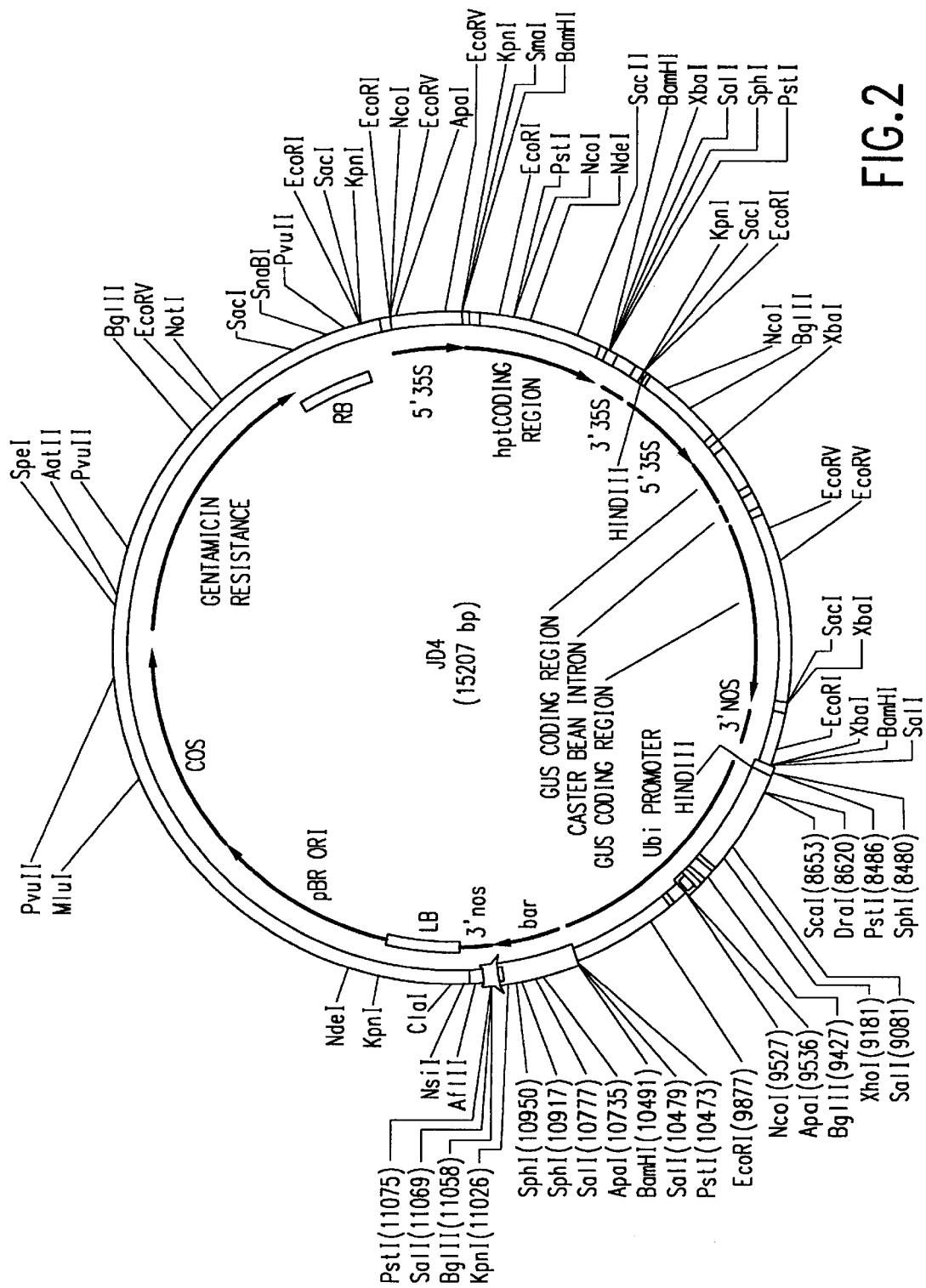
FIG. 2 is a plasmid map of pJD4. The T-DNA region of pJD4 encodes hygromycin resistance (35S-hpt-35S), Bialaphos resistance (maize ubiquitin 5' region-bar-nos) and a reporter gene construct (35S-intgus-nos).

Japonica rice cultivar Taipei 309 and Javanica rice cultivar Jefferson were used in this example. *Agrobacterium tumefaciens* strain LBA4404 (Moekema et al. (1983) *Nature* 303:179) containing the binary vector pJD4 (FIG. 2) and an extra copy of a DNA fragment encoding virulence genes from pTVK291 (Jin et al. (1987) *J. Bacteriology* 169:4417) was used for transformation. The T-DNA region of pJD4 contains selectable marker gene constructs for hygromycin resistance (35S-hpt-35S) and bialaphos resistance (maize ubiquitin 5' region-bar-nos), and an intron-containing gus reporter gene construct (35S-intgus-nos) for monitoring the transformation events.

Rice plants were grown in the greenhouse and fertilized on a weekly basis. Agrobacterium strain LBA4404 (pJD4) was grown on AB minimum media (Lichtenstein et al., "Genetic Engineering of Plants" in Glover, ed., *DNA Cloning: A Practical Approach*, vol. II, pp. 67–119, (IRL Press, Oxford (1985)) with 50 mg/L of gentamycin and 100 mg/L of kanamycin for two to three days at 28° C. The bacteria were collected and resuspended in AAM (Hiei et al. (1994) *Plant J.* 6:271) or vacuum infiltration liquid medium (Bechtold et al. (1993) C.R. Acad. Sci. Paris, *Life Sci.* 316:1194) at a concentration of 1.0–1.5 OD (550 nm) essentially as described by Bechtold et al, id. with modifications including the use of the wetting agent Silwet®L-77 (OSi Specialities) at 200, μL/L.

Inflorescences were developmentally staged according to flower size from 0.5 to 4 mm (longitudinal dimension). After dissection, the panicles were placed on callus initiation medium to provide inflorescence-derived calli, or immersed in Agrobacterium solution AAM with 100 μM acetosyringone) for about 15–20 minutes to provide Agrobacterium-treated panicles. A vacuum of 2 mm Hg was applied for 5–20 minutes to panicles immersed in Agrobacterium solution and the material was shaken several times. The Agrobacterium-treated panicles were placed on callus initiation medium containing 200 mg/L of cefotaxime. Inflorescence-derived calli were transformed using the protocol described in Dong et al. (1996) for transformation of scutellar callus. Briefly, calli were inoculated with Agrobacterium in AAM supplemented with 100 μGM acetosyringone and co-cultivated in the dark at 26° C. for 3 days. The inflorescence-derived calli were subcultured on hygromycin-containing selective medium. The expression of GUS was scored after three days of co-cultivation.

Results

Histochemical staining for GUS expression in nice inflorescences that had been vacuum infiltrated with Agrobacterium solution was performed using 5-bromo-4-chloro-3-indolyl glucuronide (X-Gluc) as a substrate essentially as described by Dong et al., id. Successful transformation required the presence of Silwet® L-77 and 100 μM acetosyringone in the co-cultivation medium. Various periods of vacuum infiltration (5–20 minutes) had no significant effect on GUS activity. As shown in Table I, histological staining revealed GUS activity in tissue from panicles bearing flowers of the 1–3 mm stages. A low frequency of GUS staining was also observed in floral stem tissue.

TABLE I

X-gluc staining of inflorescence tissue after vacuum infiltration in Agrobacterium solution and subsequent co-cultivation for three days

| Flower size (mm) | GUS expression (+/total pieces of tissue) | | |
|---|---|---|---|
| 0.5 | 0 | 0 | 0 |
| 1 | 57/173 | 45/83 | 45/105 |
| 2 | 46/93 | 68/101 | 34/127 |
| 3 | 25/121 | 17/96 | 14/98 |
| 4 | 0 | 0 | 0 |

These data demonstrate that inflorescence tissue can be successfully transformed by Agrobacterium.

EXAMPLE 2

Methods

Rice plants Taipei 309, IR72 and Jefferson were grown in the greenhouse and fertilized on a weekly basis. Agrobacterium strain LBA4404 (pJD4) was grown on AB minimum medium with 50 mg/L of gentamycin and 100 mg/L of Kanamycin for 2–3 days at 28° C. Bacteria were collected and resuspended in AAM medium or vacuum infiltration medium as described in Example 1. Inflorescences were developmentally staged according to flower size (from 0.5 to 4 mm in longitudinal dimension). After dissection, the panicles were placed in Agrobacterium solution and transformed using the protocol described in Dong et al. (1996) for transformation of scutellar callus. Briefly, untreated panicles, or panicles precultured 3–5 days on callus initiation medium, were co-cultivated with LBA4404 (pJD4) in AAM medium supplemented with 100 $\mu$M acetosyringone, for 72 hours at 26° C. The Agrobacterium-treated inflorescences were placed on callus initiation medium containing 200 mg/L of cefotaxime, and the inflorescence-derived calli were subcultured on hygromycin (50 mg/L) and cefotaxime (200 mg/L)-containing selective medium. Plants were regenerated from resistant callus tissue on MSD4 medium as described by Dong et al., id. Gene transfer was measured in several independent experiments for the GUS expression.

Genomic DNA blot analysis of rice plants transformed by LBA4404 (pJD4) were carried out using methods described in Buchholz et al (1998) in *Plant Virology Protocols: From Virus Isolation to Transgenic Resistance*, Foster et al., eds, Humana Press, Inc., Totowa, N.J., pp. 397–416.

Results

Positive evidence for transient transformation was obtained by X-gluc staining in all three cultivars tested, and stably transformed callus lines of Taipei 309 were obtained. These data indicate that the time from callus initiation to plantlet regeneration (28 to 42 days) is considerably shorter using the panicle-callus approach than for the scutellar callus method described by Dong et al., id. and Hiei et al. (1994) *Plant J* 6:271., which requires 74 days.

Figure 3A:
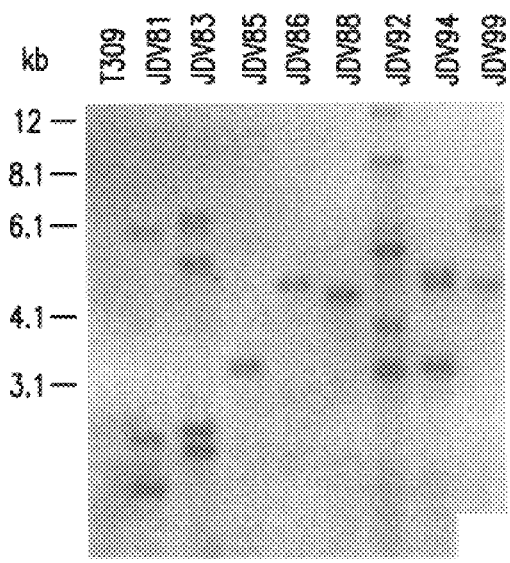
FIG. 3 depicts a genomic DNA blot analysis of transgenic rice derived from inflorescence. Two micrograms of genomic DNA were digested to completion with HindIII, electrophoresed in a 0.7% agarose gel, transferred to nitrocellulose membrane, and probed with $^{32}$P-labeled DNA sequences of hpt (Panel A) or gus (Panel B).
Figure 3B:
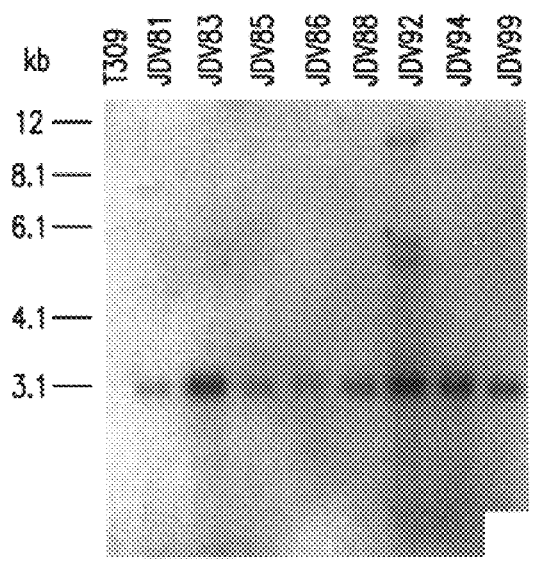

Twenty-five GUS positive plants were recovered from co-cultivation of Taipei 309 panicles with LBA4404 (pJD4). At least one GUS positive plant was regenerated from each of the resistant callus lines. These plants were established in the greenhouse and genomic DNA blot analysis conducted. Of the 25 plants from 11 independent lines transformed with LBA4404 (pJD4), eight independent transgenic lines were subjected to genomic DNA blot analysis to confirm the presence of T-DNA inserts. Two micrograms of genomic DNA were digested to completion with Hind III, electrophoresed in a 0.7% agarose gel, transferred to nitrocellulose membrane, and probed with $^{32}$P-labeled DNA sequences of hpt (FIG. 3, Panel A) or gus (FIG. 3, Panel B). In FIG. 3, Panel B shows the presence of an intact 3.1 kb Hind III DNA fragment that contains an intgus reporter gene construct, and Panel A shows right border fragments, indicating independent transformation events.

It was observed that induction of callus formation from the floral tissues was closely associated with high frequencies of transformation, indicating a beneficial effect of tissue-wounding for Agrobacterium-mediated transformation. Additionally, transformed flower tissue that callused survived on selective medium whereas those that did not callus died. The foregoing examples demonstrate that use of inflorescence provides a simpler and more rapid method for the development of transformed callus than methods utilizing scutellar-derived callus.

We claim:

1. A method of transforming a monocot comprising co-cultivating a monocot inflorescence with Agrobacterium containing a plasmid comprising a heterologous nucleic acid.

2. The method of claim 1 comprising dissecting an inflorescence from a monocot and co-cultivating the inflorescence with Agrobacterium containing a plasmid comprising a heterologous nucleic acid.

3. The method of claim 2 wherein said co-cultivating of inflorescence with Agrobacterium comprises contacting said inflorescence with a solution comprising said Agrobacterium for from about 60 to about 80 hours at 26° C.

4. The method of claim 3 wherein said solution further comprises a wetting agent and acetosyringone.

5. A method of transforming a monocot comprising dissecting an inflorescence from a monocot, initiating a callus from the inflorescence to generate an inflorescence-derived callus, and co-cultivating the inflorescence-derived callus with Agrobacterium containing a plasmid comprising a heterologous nucleic acid.

6. The method of claim 5 wherein said co-cultivating of inflorescence-derived callus with Agrobacterium comprises contacting said inflorescence-derived callus with a solution comprising said Agrobacterium for from about 60 to about 80 hours at 26° C.

7. The method of claim 6 wherein said solution further comprises a wetting agent and acetosyringone.

8. The method of claim 1 or 5 wherein said monocot is a member of the family Gramineae.

9. The method of claim 8 wherein said monocot is selected from the group consisting of rice, corn, wheat, barley, oats and rye.

10. The method of claim 1 or 5 wherein said Agrobacterium is *Agrobacterium tumifaciens* or *Agrobacterium rhizogenes*.

11. The method of claim 1 or 5 wherein said Agrobacterium is *Agrobacterium tumifaciens*.

12. The method of claim 11 wherein said *Agrobacterium tumifaciens* contains a binary vector comprising said heterologous nucleic acid.

13. A method of making a transgenic monocot comprising dissecting an inflorescence from a monocot, initiating a callus from the inflorescence to generate an inflorescence-derived callus, co-cultivating the inflorescence-derived callus with Agrobacterium containing a plasmid comprising a heterologous nucleic acid, and regenerating a transgenic monocot from the callus.

14. The method of claim 13 wherein said co-cultivating of inflorescence-derived callus with Agrobacterium comprises contacting said inflorescence-derived callus with a solution comprising said Agrobacterium for from about 60 to about 80 hours at 26° C.

15. The method of claim 14 wherein said solution further comprises a wetting agent and acetosyringone.

16. A method of making a transgenic monocot comprising dissecting an inflorescence from a monocot, co-cultivating the inflorescence with Agrobacterium containing a plasmid comprising a heterologous nucleic acid, initiating a callus from the inflorescence and regenerating a transgenic monocot from the callus.

17. The method of claim 16 wherein said co-cultivating of inflorescence with Agrobacterium comprises contacting said inflorescence with a solution comprising said Agrobacterium for from about 60 to about 80 hours at 26° C.

18. The method of claim 17 wherein said solution further comprises a wetting agent and acetosyringone.

19. The method of claim 13 or 16 wherein said monocot is a member of the family Gramineae.

20. The method of claim 19 wherein said monocot is selected from the group consisting of rice, corn, wheat, barley, oats and rye.

21. The method of claim 13 or 16 wherein said Agrobacterium is *Agrobacterium tumifaciens* or *Agrobacterium rhizogenes*.

22. The method of claim 13 or 16 wherein said Agrobacterium is *Agrobacterium tumifaciens*.

23. The method of claim 22 wherein said *Agrobacterium tumifaciens* contains a binary vector comprising said heterologous nucleic acid.

24. A transgenic monocot produced by the method of claim 13 or 16.

25. The seeds of the transgenic monocot of claim 24.

26. Progeny of the transgenic monocot of claim 24.

* * * * *